United States Patent [19]
Collins et al.

[11] Patent Number: 6,107,083
[45] Date of Patent: Aug. 22, 2000

[54] OPTICAL OXIDATIVE ENZYME-BASED SENSORS

[75] Inventors: Thomas C. Collins, Linwood, Mich.; Christiane Munkholm, Salem; Rudolf E. Slovacek, Norfolk, both of Mass.

[73] Assignee: Bayer Corporation, E. Walpole, Mass.

[21] Appl. No.: 09/137,616

[22] Filed: Aug. 21, 1998

[51] Int. Cl.[7] .................................................. C12M 1/34
[52] U.S. Cl. ................... 435/288.7; 435/7.91; 435/14; 435/287.8; 422/56; 422/57; 422/60
[58] Field of Search .......................... 422/52, 55, 56, 422/57, 60, 82.05, 82.06, 82.07, 82.08; 436/95, 169, 170, 172; 435/7.91, 14, 287.8, 288.7; 356/39; 128/633, 634

[56] References Cited

U.S. PATENT DOCUMENTS

| | | | |
|---|---|---|---|
| 2,761,417 | 9/1956 | Russell et al. | 118/410 |
| 3,992,158 | 11/1976 | Przybylowicz et al. | 23/253 |
| 4,003,707 | 1/1977 | Lübbers et al. | 23/232 |
| 4,042,335 | 8/1977 | Clément | 23/253 |
| 4,356,149 | 10/1982 | Kitajima et al. | 422/56 |
| 4,476,870 | 10/1984 | Peterson et al. | 128/634 |
| 4,587,101 | 5/1986 | Marsoner et al. | 422/56 |
| 4,645,744 | 2/1987 | Charlton et al. | 436/74 |
| 4,649,123 | 3/1987 | Charlton et al. | 436/79 |
| 4,670,218 | 6/1987 | Gantzer et al. | 422/56 |
| 4,680,268 | 7/1987 | Clark, Jr. | 435/291 |
| 4,689,309 | 8/1987 | Jones | 436/95 |
| 4,716,363 | 12/1987 | Dukes et al. | 324/77 |
| 4,734,375 | 3/1988 | Charlton | 436/74 |
| 4,752,115 | 6/1988 | Murray, Jr. et al. | 350/96.29 |
| 4,781,890 | 11/1988 | Arai et al. | 422/56 |
| 4,810,655 | 3/1989 | Khalil et al. | 436/138 |
| 4,824,789 | 4/1989 | Yafuso et al. | 436/68 |
| 4,857,472 | 8/1989 | Wolfbeis | 436/122 |
| 4,861,727 | 8/1989 | Hauenstein et al. | 436/136 |
| 4,895,156 | 1/1990 | Schulze | 128/634 |
| 4,895,704 | 1/1990 | Arai et al. | 422/57 |
| 4,919,891 | 4/1990 | Yafuso et al. | 422/58 |
| 4,974,929 | 12/1990 | Curry | 350/96.29 |
| 5,030,420 | 7/1991 | Bacon et al. | 422/82.07 |
| 5,043,286 | 8/1991 | Khalil et al. | 436/136 |
| 5,047,350 | 9/1991 | Switalski et al. | 436/136 |
| 5,075,127 | 12/1991 | Yafuso et al. | 427/2 |
| 5,081,041 | 1/1992 | Yafuso et al. | 436/68 |
| 5,081,042 | 1/1992 | Yafuso et al. | 436/68 |
| 5,091,800 | 2/1992 | Offenbacher et al. | 359/350 |
| 5,127,405 | 7/1992 | Alcala et al. | 128/633 |
| 5,173,432 | 12/1992 | Lefkowitz et al. | 436/138 |
| 5,190,729 | 3/1993 | Hauenstein et al. | 422/91 |
| 5,208,147 | 5/1993 | Kagenow et al. | 435/14 |
| 5,281,825 | 1/1994 | Berndt et al. | 250/458.1 |
| 5,298,144 | 3/1994 | Spokane | 204/403 |
| 5,326,531 | 7/1994 | Hahn et al. | 422/82.06 |
| 5,341,805 | 8/1994 | Stavridi et al. | 128/633 |
| 5,352,348 | 10/1994 | Young et al. | 204/153.12 |
| 5,387,329 | 2/1995 | Foos et al. | 204/415 |
| 5,387,525 | 2/1995 | Munkholm | 436/111 |
| 5,453,248 | 9/1995 | Olstein | 422/82.07 |
| 5,462,858 | 10/1995 | Bale Oenick et al. | 435/16 |
| 5,462,879 | 10/1995 | Bentsen | 436/136 |
| 5,464,777 | 11/1995 | Yip | 436/98 |
| 5,494,562 | 2/1996 | Maley et al. | 204/403 |
| 5,506,148 | 4/1996 | Munkholm | 436/111 |
| 5,520,883 | 5/1996 | Charlton et al. | 422/56 |
| 5,601,694 | 2/1997 | Maley et al. | 204/415 |
| 5,605,152 | 2/1997 | Slate et al. | 128/634 |
| 5,624,847 | 4/1997 | Lakowicz et al. | 436/68 |
| 5,631,340 | 5/1997 | Olstein | 528/59 |

FOREIGN PATENT DOCUMENTS

| | | | |
|---|---|---|---|
| 0105870 | 10/1983 | European Pat. Off. | G01N 33/84 |
| 0119861 | 11/1987 | European Pat. Off. | G01N 33/72 |
| 0 409 033 A2 | 7/1990 | European Pat. Off. | |
| 0409033 | 7/1990 | European Pat. Off. | G01N 21/64 |
| 0442276 | 1/1991 | European Pat. Off. | A61B 5/00 |
| 409032 | 1/1991 | European Pat. Off. | C12Q 1/00 |
| 0142849 | 8/1992 | European Pat. Off. | G01N 33/52 |
| 0287328 | 10/1993 | European Pat. Off. | C07D 498/08 |
| 0287327 | 7/1994 | European Pat. Off. | C07D 498/08 |
| 4323277 | 1/1994 | Germany | G01N 21/76 |
| 87/00023 | 1/1987 | WIPO | A61B 5/00 |
| 90/07107 | 6/1990 | WIPO | G01N 21/64 |
| 92/19957 | 11/1992 | WIPO | G01N 21/76 |
| 95/08107 | 3/1995 | WIPO | G01N 21/63 |
| 95/10522 | 4/1995 | WIPO | C07D 487/22 |
| 95/26501 | 10/1995 | WIPO | G01N 31/22 |
| 95/30148 | 11/1995 | WIPO | G01N 31/22 |
| 97/37210 | 10/1997 | WIPO | G01N 21/64 |
| 98/15645 | 4/1998 | WIPO | C12Q 1/22 |

OTHER PUBLICATIONS

Aartsma, T. et al., "Porphyrins.43. Triplet Sublevel Emission of Platinum Tetrabenzoporphyrin by Spectrothermal Principal Component Decomposition"; *J. Am. Chem. Soc.* 104, pp. 6278–6283 (1982).

Brandrup, J. et al., "Permeability and Diffusion Data" Polymer Handbook, 3rd edition, pp. VI/435–VI/449, John Wiley and Sons, New York, NY (1989).

(List continued on next page.)

*Primary Examiner*—David A. Redding

[57] ABSTRACT

The invention discloses enzyme-based optical sensors for detecting blood components which are substrates for oxidative enzymes, the sensors advantageously employing a multiple-layer structure featuring a thin, rapidly responding, optical, oxygen sensing layer. The sensors comprise, in order, a) an enzymatic layer containing an oxidative enzyme or enzyme cascade in a water and oxygen-permeable matrix; b) an oxygen sensing layer containing luminescent dye in a light-transmissive, oxygen-permeable matrix; and which is preferably deposited onto c) a light-transmissive substrate. Embodiments of the invention may further include a rapidly hydrating gas-permeable cover, or spacer, layer deposited over the enzymatic layer. A particulate filler material may be included in an effective amount in the oxygen sensing layer to reduce sample light scattering effects. The sensors of the disclosure may be used to detect creatinine and other enzyme-oxidizable analytes such as glucose, lactate or cholesterol, and may be made easily using standard coating techniques known in the art. These sensors are suitable for multiple analyses, but the materials and methods used allow the sensors to be disposable as well, allowing their wide use in medical and analytical applications.

22 Claims, 10 Drawing Sheets

OTHER PUBLICATIONS

Bruno, et al., "All–Solid–State Miniaturized Fluorescence Sensor Array for the Determination of Critical Gases and Electrolytes in Blood" *Anal. Chem.* 69, pp. 507–513 (1997).

Demas, J. et al., "Design and Applications of Highly Luminescent Transition Metal Complexes"; *Analytical Chemistry*, vol. 63, No. 17; pp. 829–837 (1991).

Kautsky, V. et al., "Nachweis geringster Sauerstoffmengen durch Phosphoreszenztilgung", *Zeitschrift für anorganische und allgemeine Chemie, Band* 222, pp. 126–134 (1935). (German).

Kautsky, V. et al., "Luminescenzumwandlung durch Sauerstoff Nachweis geringster Sauerstoffmengen", *Zeitschrift Naturforschung* 2a, pp. 167–172 (1947). (German)

Klimant, I. et al., "Oxygen–Sensitive Luminescent Materials Based on Silicone–Soluble Ruthenium Diimine Complexes" *Anal. Chem.* 67 pp. 3160–3166 (1995).

Lui, Hsue–Yang et al., "Oxygen Permeability of Sol–Gel Coatings" *Applied Spectroscopy*, vol. 46, No. 8 pp. 1266–1272 (1992).

MacCraith et al., "Optical Chemical Sensors Based on Sol–Gel Materials: Recent Advances and Critical Issues", *J. Sol–Gel Sci. and Tech.*, vol. 8, pp. 1053–1061 (1997).

Papkovsky et al., "Phosphorescent Complexes of Porphyrin Ketones: Optical Properties and Application to Oxygen Sensing", *Anal. Chem.* 67, pp. 4112–4117 (1995).

Papkpvsky et al., "Phosphorescent Polymer Films for Optical Oxygen Sensors", *Biosensors & Electronics* 7, pp 199–206 (1991).

Roffey, "Photopolmerization of Surface Coatings", *Wiley–Interscience,* p. 110–117 (1985).

Salame, M. "Transport Properties of Nitrile Polymers", *J. Polymer Sci. Symp.* 41, pp 1–15 (1973).

Stern, V. et al., "Uber die Abklingungszeit der Fluorreszenz", *Physik. Zeitschr.* XX; pp. 183–188 (1919). (German).

Vinogradov et al., "Metallotetrabenzoporphyrins. New Phosphorescence Probes for Oxygen Measurements", *J. Chem. Soc. Perkin Trans.* 2, pp. 103–111 (1995).

Watts, R.J., et al., "Spectroscopic Characterization of Complexes of Ruthenium (II) and Iridium (III) with 4,4'–Diphenyl–2,2'–bipyridine and 4,7–Diphenyl–1,10–phenanthroline", *J. Am. Chem. Soc.* 93, pp. 3184–3188 (1971).

Yang et al., "Oxygen Permeability Coefficients of Polymers for Hard and Soft Contact Lens Applications", *J. Membrane Sci.* 9, pp. 53–67 (1981).

OPTICAL OXIDATIVE ENZYME-BASED SENSORS

BACKGROUND OF THE INVENTION

This invention generally relates to instrumentation for sensing various blood analytes, and more particularly towards optical sensors for detecting blood components which are substrates for oxidative enzymes.

Various sensors have been described in the art for measuring the presence of a substrate which may be enzymatically oxidized. Permanent or multiple use sensors have been made, for example, as in U.S. Pat. No. 5,494,562, disclosing an electrochemical glucose sensor wherein the enzyme glucose oxidase is co-immobilized in a platinized carbon paste in contact with an electrode. The paste is further covered with a semipermeable porous polymer to permit the movement of hydrated glucose and oxygen gas to the paste, where the active enzyme converts these substrates to peroxide and gluconate. The polarized electrode then delivers a current and the reoxidation of peroxide to oxygen may be measured amperometrically. Examples of other amperometric sensor technologies have been described in U.S. Pat. Nos. 4,680,268, 5,352,348, and 5,298,144. These sensors are disadvantageous for use in disposable applications, because they were designed to function in a multiuse format with an elaborate instrument system, and they employ expensive materials and methods of manufacture as well as requiring wet up and calibration before use.

Another example of permanent or multiple use sensors, using fiber optic glucose sensors, is disclosed in U.S. Pat. No. 4,974,929, describing a chamber filled with an oxygen quenchable dye at the end of a fiber surrounded by a double jacketed wall. Sandwiched between the wall jackets is a crosslinked polymer layer containing the enzyme glucose oxidase. The glucose and oxygen consumption at the cylinder wall lowers oxygen diffusion into the cylinder space. This sensor requires a fair degree of manual assembly and is also not suitable for inexpensive, routine single use measurement applications. Each sensor must also be individually calibrated before use, and employs a large cylindrical volume for dye equilibration and accordingly suffers in response speed due to the requirement for bulk equilibration effects.

Disposable or "one-shot" sensors, on the other hand, have been disclosed also, such as the colorimetric sensor set forth in U.S. Pat. No. 5,208,147. Disposable dry reagent strips, e.g., U.S. Pat. Nos. 3,992,158, 4,689,309, and 5,520,883, were developed specifically for single use applications. In operation, the sample hydrates the test strip and reagents are consumed in the development of a colorimetric change based on peroxide chemistries. They can be stored dry, are ready to use on demand, and find use in "wet" blood or serum chemistry, where the strips become saturated during use. However, the hydration and depletion of reactive chemical reagents in these strips effectively prevents their re-use. Handling and biohazard disposal of the many individually used test elements that would routinely be generated is a drawback.

In the development of optical sensors which are inexpensive to manufacture and may be used in a rapid point of care setting, optical coatings and membranes containing luminescent dyes on light-transmissive substrates for the detection and measurement of $O_2$ in blood, have been developed and are incorporated by reference as U.S. application Ser. No. 08/617,714. An advantage of these sensors is that it is possible to bring the sensor into intimate contact with a blood sample while transmitting excitation light through the transparent substrate from the "back" side of the sensor, to enable subsequent detection of the luminescent radiation emitted from the luminescent dye from the same side of the sensor. Such coatings or membranes are quite thin, typically 1–5 $\mu$m for pH and oxygen sensors, and show an extremely rapid response.

However, the application of such thin optical coating-based technologies to the area of glucose determination is not straightforward. Firstly, measurements of oxygen uptake in blood are directly affected by the oxygen buffering capacity of a blood sample itself. If blood is introduced into a measurement system containing an optical sensor, red blood cells (RBCs) will be in contact with the sensor. Since the principal of operation of optical glucose sensors is based on oxidization of available glucose in the blood sample by immobilized glucose oxidase in the sensor (i.e., the detection of oxygen is directly correlatable to the glucose concentration), the depletion of oxygen proximate to the membrane will be high. As such, red blood cells (RBCs) in contact with the sensor will sense the low oxygen concentration at the membrane surface and respond by releasing bound oxygen, thus acting as an oxygen buffer and skewing the results obtained.

Secondly, a large fraction of the excitation light (in some cases as much as 90–95%) as well as the luminescent energy emitted from the sensing layer from these thin membranes passes into the sample (blood) to be absorbed, scattered, or reflected back into the sensing layer and into the detection optics. These effects can, together, produce a four-fold change in luminescence signal level between a perfectly absorbing and perfectly reflecting sample, thus presenting a significant source of uncertainty in the use of luminescent optical sensors, particularly if used in the simplest amplitude readout mode.

Accordingly, it has been desired to obtain optical sensors for measuring oxidizable analytes which are inexpensive enough to design and manufacture to make them disposable, avoid the aforementioned drawbacks, and also allow multiple uses if desired.

SUMMARY OF THE INVENTION

The presently-disclosed invention relates to enzyme-based optical sensors for detecting blood components which are substrates for oxidative enzymes, the sensors advantageously employing a multiple-layer structure featuring a thin, rapidly responding, optical, oxygen sensing layer. In one embodiment, the sensor comprises, in order, a) a rapidly hydrating gas-permeable cover, or spacer, layer; b) an enzymatic layer containing an oxidative enzyme also in a water and oxygen-permeable matrix; c) an oxygen sensing layer containing luminescent dye in a light-transmissive, oxygen-permeable matrix; and, preferably, d) a light-transmissive substrate. In another embodiment the oxygen sensing layer further comprises an effective amount of a particulate filler material to reduce or eliminate sample light scattering effects. The inventive sensors may be used to detect glucose and other enzyme-oxidizable analytes such as lactate or cholesterol.

In yet another embodiment, the sensor additionally comprises, an enzyme "cascade" system instead of a single oxidative enzyme in the enzymatic layer containing a water and oxygen-permeable matrix. These sensors may be employed to detect analytes such as creatinine, which may not be enzymatically oxidized by a single enzyme but require several enzymatic steps to generate an oxidizable analyte derivative.

The sensors of this disclosure may be made easily using standard coating techniques known in the art. The sensors are adaptable for reuse, but available materials and methods allow the sensors to be disposable as well, permitting their wide use in medical and analytical applications.

BRIEF DESCRIPTION OF THE DRAWINGS

The invention will be further understood by reference to the disclosure and the attached drawings, of which.

DETAILED DESCRIPTION OF THE INVENTION

"Polymeric sensing layer", as used herein, refers to articles such as membranes or thin detection layers made of a composition which exhibits the quenching of luminescent energy by a gas such as oxygen ($O_2$), and can be used for quantitative and qualitative determination of the gas concentration in the environment being measured. The sensing layer or membrane comprises a polymeric material containing at least one luminescent dye species preferably well-dispersed in the polymeric material.

"Luminescence", as used herein, means light emitted from a molecule by radiative dissipation of energy from an electronically excited state. "Fluorescence", as used herein, means luminescence resulting from the transition between states of identical multiplicity, typically between the lowest excited singlet state and the singlet ground state of the molecule. "Phosphorescence", as used herein, means luminescence resulting from the transition between states of differing multiplicity, typically between the lowest excited triplet state and the singlet ground state.

"Light-transmissive materials", as used herein, refers to materials preferably transmitting at least about 95% of electromagnetic radiation used to induce electronic excitations in luminescent material which result in emissions, more preferably at least about 99% as measured by the transmission mode.

Figure 1:
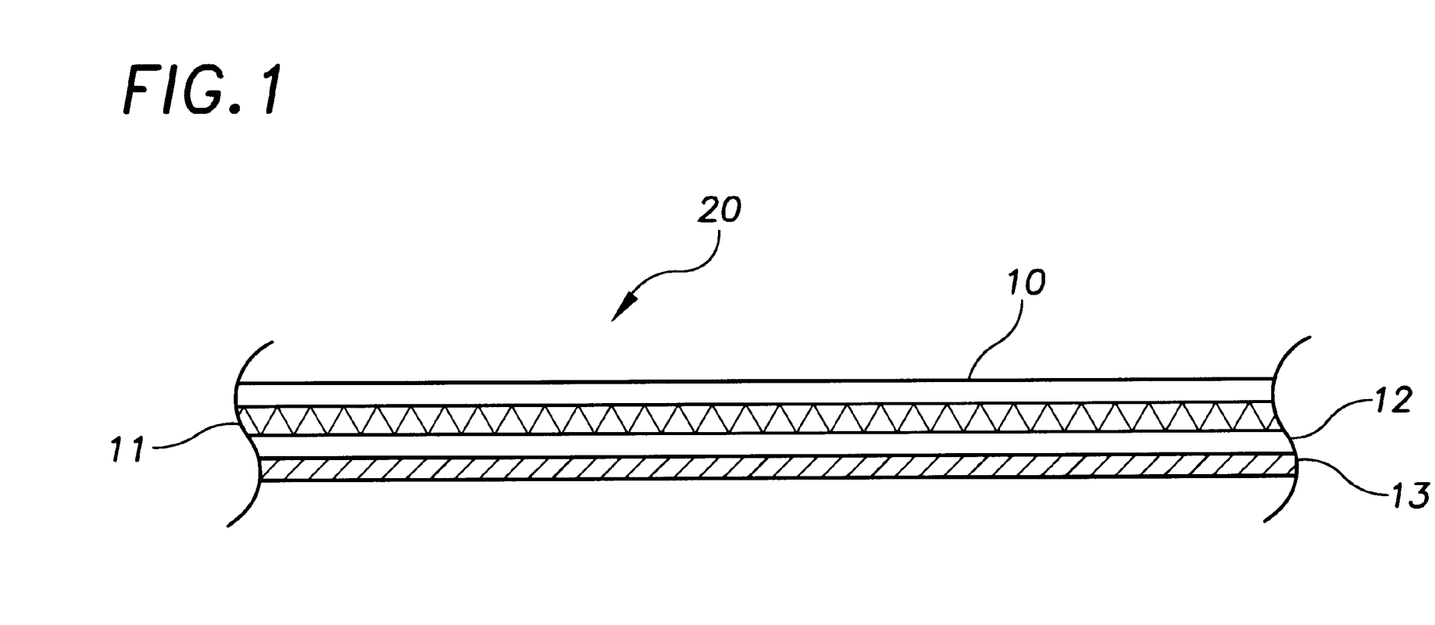
FIG. 1 is a cross-sectional view of a sensor in accordance with one embodiment of the presently disclosed invention.

FIG. 1 depicts an embodiment of an optical sensor 20 in accordance with the disclosure in simplified cross-sectional view. Sensor 20 comprises (from top to bottom) a rapidly hydrating gas-permeable cover layer 10; an enzymatic layer 11 containing an oxidative enzyme also in a water permeable and oxygen-permeable matrix; an oxygen sensing layer 12 containing luminescent dye in a light-transmissive, oxygen-permeable matrix; and a light-transmissive substrate 13. Further description of each layer is set forth below.

The light transmissive substrate 13 is preferably supplied to provide a surface for deposition of the other layers of the oxidative enzyme sensor. It must be light transmissive to allow the excitation radiation from a source situated on the uncoated side of the substrate to pass to the oxygen sensing layer 12, and the luminescent energy emitted from the oxygen sensing layer 12 pass back to the detection optics also situated on the uncoated side of the substrate. The substrate should have a relatively low permeability to gases, especially oxygen, so as not to significantly influence the response of the oxygen sensing layer. An exemplary and nonlimiting list of suitable substrates includes MYLAR®; polyethyleneterephthalate (PET); SARAN®; and glass. The substrate may be flexible or rigid, according to the particular demands of the desired end use. The light-transmissive substrate is preferably polymeric and has a permeability of at most about 0.05 Barrers, more preferably at most about 0.005 Barrers, and most preferably at most about 0.0005 Barrers, as measured by the methods disclosed in *J. Membrane Sci.* 9, 53 (1981). Other suitable materials will be apparent to those of ordinary skill in the art and are intended to be within the scope of the present invention.

The oxygen sensing layer 12 contains luminescent dye in a light-transmissive, oxygen-permeable matrix. Any luminescent dyes capable of excitation, oxygen-quenchable emission, and which may be readily dispersed within the chosen matrix material, may be used. Dyes which may be used in the present invention include, but are not limited to: metal complexes of ruthenium (II), osmium (II), iridium (III), rhodium (III) and chromium (III) ions complexed with 2,2'-bipyridine; 1,10-phenanthroline; 4,7-diphenyl-1,10-phenanthroline; 4,7-dimethyl-1,10-phenanthroline; 4,7-disulfonated-diphenyl-1,10-phenanthroline; 5-bromo-1,10-phenanthroline; 5-chloro-1,10-phenanthroline; 2-2'bi-2-thiazoline; 2,2'-bithiazole, and other a-diimine ligands as disclosed in, e.g., U.S. Pat. No. 4,752,115 and U.S. Pat. No. 5,030,420; and porphyrin, chlorin or phthalocyanine complexes of $VO^{2+}$, $Cu^{2+}$, $Zn^{2+}$, $Pt^{2+}$ and $Pd^{2+}$ such as is disclosed in U.S. Pat. Nos. 4,810,655 and 5,043,286 and International application number PCT/EP97/03915. Note that a particular fluorescent dye material may be synthesized for a particular use with a given polymeric material based on the desired $K_{sv}$ (i.e., Stern-Volmer constant) of the polymeric sensing membrane. Specific luminescent dye molecules which may be used include tris-(4,7-diphenyl-1,10-phenanthroline) Ru (II); octaethyl-Pt-porphyrin; octaethyl-Pt-porphyrin ketone; tetrabenzo-Pt-porphyrin; tetraphenyl-Pt-porphyrin; meso-tetraphenyl-tetrabenzo-Pt-porphyrin; tetracyclohexenyl-Pt-porphyrin; octaethyl-Pt-chlorin; and tetraphenyl-Pt-chlorin.

In an embodiment, the light-transmissive, oxygen-permeable matrices may comprise a copolymer made by selecting a first homopolymer comprised of first monomeric units, the first homopolymer having a first oxygen permeability value; selecting a second homopolymer comprised of second monomeric units, the second homopolymer having a second oxygen permeability value that is higher than the first permeability value; and copolymerizing the first and second monomeric units to obtain a copolymer having an intermediate oxygen permeability value, i.e., between the first and second permeabilites values, the intermediate permeability providing the desired permeability for the desired oxygen sensing formulation, such as described in copending and commonly assigned U.S. patent application Ser. No. 09/010, 161, Attorney Docket No. CCD-239XX, the entire disclosure of which is incorporated herein by reference.

In another embodiment, the oxygen sensing layer may further comprise a particulate filler material, in an amount effective to prevent the influence of changes in the sample absorbance and reflectance characteristics as disclosed in U.S. application Ser. No. 09/009,914 and incorporated herein by reference. The filler material appears to effectively eliminate light transmission through the sensor. Inclusion of the scattering filler is particularly advantageous for measurements involving luminescence amplitude or amplitude ratios. Accordingly, particles of, e.g., $TiO_2$, zinc oxide, antimony trioxide, barium sulfate, magnesium oxide, and mixtures thereof, and in particular, $TiO_2$ or $BaSO_4$, may be added in a range of 0 to about 95 wt. % (based on the total weight of the oxygen sensing layer material), preferably 1 to 50 wt. %, and more preferably 5 to 50 wt. %.

The oxygen sensing layer 12 is deposited, preferably, as a continuous layer, e.g., as a membrane, on light-transmissive substrate 13. Standard coating techniques known in the art, such as described in the Examples herein, may be used.

The enzymatic layer 11 includes an oxygen consuming or oxidase based enzyme in an oxygen-permeable matrix which is rapidly hydrated and, which is deposited on the oxygen-sensing layer 12. (By "rapidly hydrating" is meant that water is absorbed rapidly, to enable ions and small charged or water soluble molecules to diffuse through the membrane at about the diffusion speed of the water.) Rapidly hydrating materials which may be used to embed the enzyme in the enzyme layer include poly (vinyl alcohol) or (PVOH), crosslinked poly(vinyl alcohol) or (x-PVOH), hydrophylic polyurethanes, polyacrylamides or gelatin. The matrix of the enzyme layer 11 should, after hydration, be freely permeable to water and to the substrates of the oxidase enxyme e.g. oxygen and glucose for example, but it is not necessary that the matrix be light-transmissive. One advantage of the sensors of this disclosure is that the enzymatic layer need not also function as a "light shield", i.e., attenuate the effects of sample light scattering as described hereinabove. Instead, the enzymatic layer can be specifically optimized to pass substrates and products, e.g., glucose lactate creatinine and oxygen, to the immobilized enzymes in the enzymatic layer, and preserve the enzymes in an active state.

The optical enzyme-based sensors of this disclosure are usefull for measuring the concentration of analytes which are substrates of the immobilized oxidative enzymes. Such enzymes include, without limitation, glucose oxidase, cholesterol oxidase, lactate oxidase and sarcosine oxidase.

The enzymatic layer may also comprise an enzyme mixture, such as an enzyme cascade, which allows for the detection of analytes which cannot directly, practically or possibly be the subject of enzymatic oxidation, such as creatinine. Creatinine is an end product of nitrogen metabolism. In healthy individuals, creatinine is transported from blood to urine by the kidney glomeruli and then excreted in the urine without reabsorption. As such, creatinine is an important diagnostic index of kidney function and muscle diseases. By providing an enzyme cascade system comprising, e.g., creatinine amidohydrase ("CA"), creatine amidinohydrolase ("CI"), and sarcosine oxidase ("SO"), creatinine is enzymatically converted to glycine, formaldehyde and hydrogen peroxide as follows:

In the final reaction, the depletion of oxygen or ($O_2$) is measurable by the oxygen sensing layer. Thus, the amount of creatinine in the sample (being directly proportional to the amount of sarcosine oxidized) may be quantitatively determined.

Another embodiment of the present invention includes a rapidly hydrating cover or spacer layer 10 over the enzymatic layer 11. Cover layer 10 ensures more accurate oxygen readings, i.e., those which are not skewed by oxygen concentration effects caused by red blood cell contact with the sensor. As blood is introduced into a system containing an optical sensor as disclosed herein, red blood cells (RBCs) will be in contact with the sensor, i.e., at cover layer 10. Since the principal of operation of the present application is based on the oxidization, e.g., of available glucose in the blood sample by the immobilized glucose oxidase (i.e., the detection of oxygen is directly correlated to the glucose concentration), the depletion of oxygen proximate to the membrane will be high. Without cover layer 10, red blood cells (RBCs) in contact with the sensor will respond to the low oxygen level at the enzyme layer surface and release their bound oxygen, thus skewing the results obtained. However, provision of a spacer layer 10 over the enzymatic layer 11 ensures that any oxygen released from the RBCs that are proximate to the spacer layer 10 is forced to follow a longer diffusion path than the dissolved oxygen from the blood plasma brought into the membrane sensor under short term "wet up" and normal measurement conditions. The RBCs are therefore, through equilibrium concentration effects, effectively delayed or prevented from "dumping" their payload of oxygen into the membrane to counter the loss of oxygen immediately adjacent to the oxygen sensor layer. Accordingly, as the blood sample passes over sensor 20, the oxygen concentration in the blood sample remains unchanged for a period of time sufficient for measurement to take place. Suitable material for the spacer layer includes poly(vinyl alcohol), which may be preferably crosslinked for chemical and physical durability. Other suitable materials include any of the rapidly hydrating materials which may be used in used in the enzyme layer 11 itself.

Figure 8:
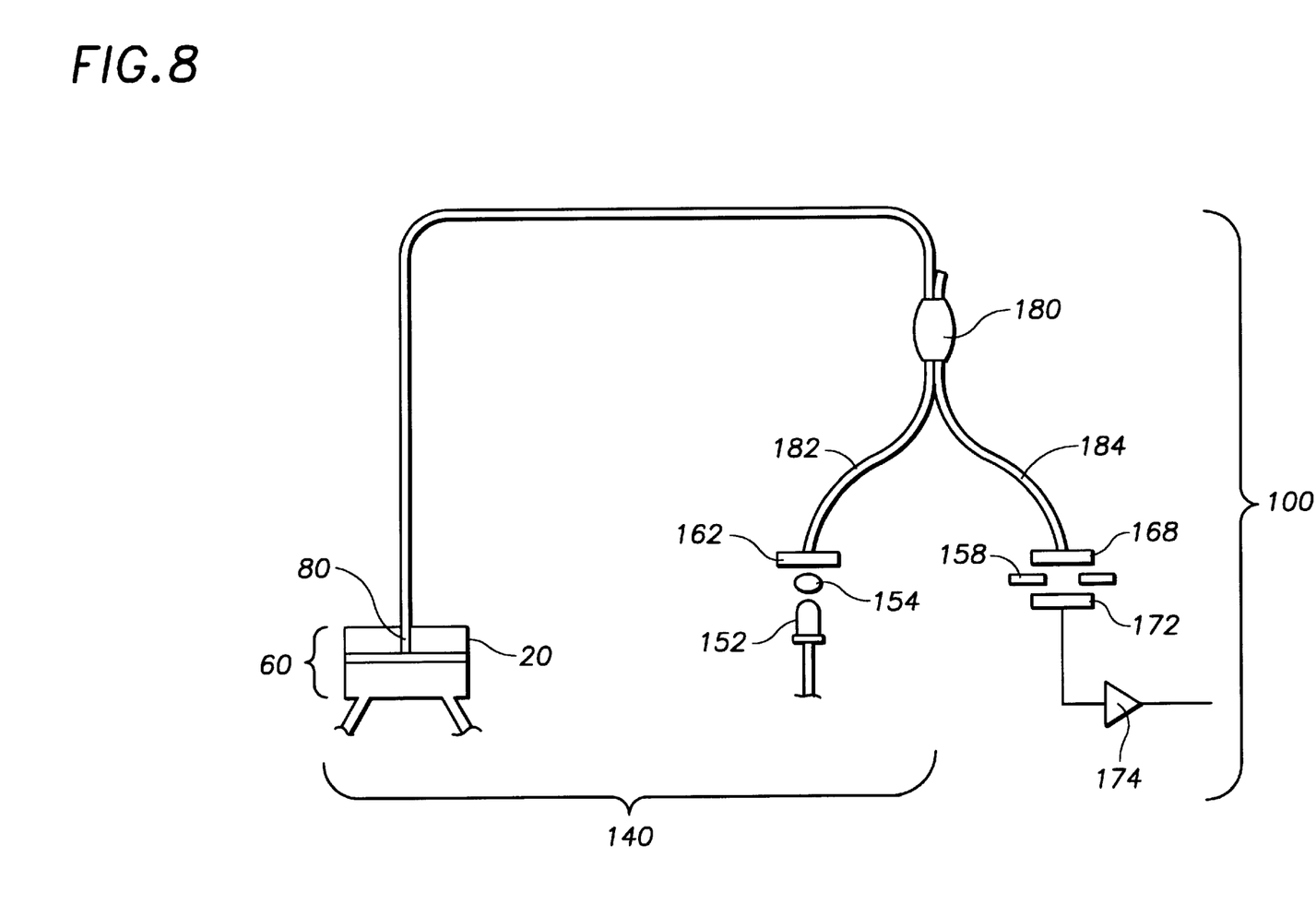
FIG. 8 is a schematic representation of a test apparatus for measuring an output signal amplitude of a luminescent optical sensor as described herein.

In operation of the inventive sensors, FIG. 8 describes a suitable device for measuring the luminescent amplitude response of optical sensors 20 in the present invention. The measurement apparatus 140 is comprised of a flow cell assembly 60 and a source and detector sub-system 100. For the optical source and detector sub-system 100, LED source 152 and lens 154 direct excitation light through filter 162 into one leg 182 of fiber optic splitter 180 (e.g., from American Laubscher Corp., Farmingdale, N.Y.). The luminescent light signal returning from the sensor 20 through fiber cable 80 and leg 184 is passed through filter 168 and aperture 158 before detection by photodiode 172 (e.g., from Hamamatsu Corporation, Bridgewater, N.J.). The output current of emission detector 172 is amplified with a preamplifier 174, such as a Stanford Research SR570 current preamplifier (Stanford Research Systems, Inc., Sunnyvale, Calif.), and converted to a voltage and recorded for use in analysis.

For example, with the luminescent dye meso-tetraphenyl--tetrabenzo-Pt-porphyrin ( m-TPTBP), a super bright orange LED (TLOH180P available from Marktech International Corp, Latham, N.Y.) was used for source 152. An interference filter with a 580 nm center wavelength and 100 nm half bandwidth (e.g., from Omega Optical, Brattleboro, Vt.) was used for filter 162 and a 710 EFLP long wavelength pass filter for emission above 710 nm (Omega Optical, Brattleboro, Vt.) was used for filter 168. Each individual sensor detection layer 14, employing a different dye, such as octaethyl-Pt-porphyrin (OEP) as the luminescent material 2, will typically require its own preferred LED source 152, excitation filter 162 and emission filter 168.

When the sensor detection layer 14 of optical sensor 20 is brought in contact with the sample by means of flow cell assembly 60, the optical emission signal that is generated and subsequently conveyed by fiber optic 80 to the source and detector sub-system 100 will be representative of the luminescent amplitude response. For frequency-based measurements one may employ the apparatus described in U.S. patent application Ser. No. 08/617,714.

The following illustrative and nonlimiting examples are intended to demonstrate certain aspects of the present invention.

EXAMPLE 1

Glucose sensors were made in several steps. In a first step, an oxygen sensing layer was prepared and coated on a light transmissive substrate as follows. Starting monomers were either recrystallized from bulk or freshly distilled to ensure purity. The comonomer mixture comprised of styrene (58%) and acrylonitrile (42%), and an effective amount, about 0.070 g, of the initiator azo-bis-isobutyronitrile (MW= 192.3) were dissolved in tetrahydrofuran (THF) to form a homogeneous solution. A form was made by separating the faces of two glass plates about 2 mm apart and providing a rubber sealing gasket therebetween, providing a space in the gasket to allow material to be added to the form. The form was filled with about 32 g of the above solution and heated to 60° C. for 42 hours in a dry box flushed with nitrogen. The mixture was polymerized to form a solid, then the material was removed and dissolved in about 150 ml of chloroform, glass filtered, and precipitated by adding the chloroform solution to 4 l of methanol. The precipitate was dried in a vacuum at 40° C. for three days. 2 mg of the dye octaethyl-Pt-porphyrin dye (OEP) and 100 mg of the styrene/ acrylonitrile copolymer was dissolved in 1 ml of tetrahydrofuran (THF) and a thin membrane was spin cast onto a clear MYLAR® substrate from 20 seconds at 2000 RPM.

In a second step an enzymatic layer comprising glucose oxidase was made and deposited onto the oxygen sensing layer as follows. 2 mg of glucose oxidase was dissolved in 200 mg of deionized water. 1.8 g of a methanol solution of a random copolymer made from starting monomers N,N-dimethylacrylamide (15%) and N-tert-butylacrylamide (85%) monomers was added to the glucose oxidase solution, to provide a homogenous, pale yellow solution upon vortexing. The enzyme layer was formed by spin casting the pale yellow solution on the oxygen sensing layer for 20 seconds at 2000 RPM. The finished sensors were dried at room temperature under vacuum for three hours before testing.

Figure 2:
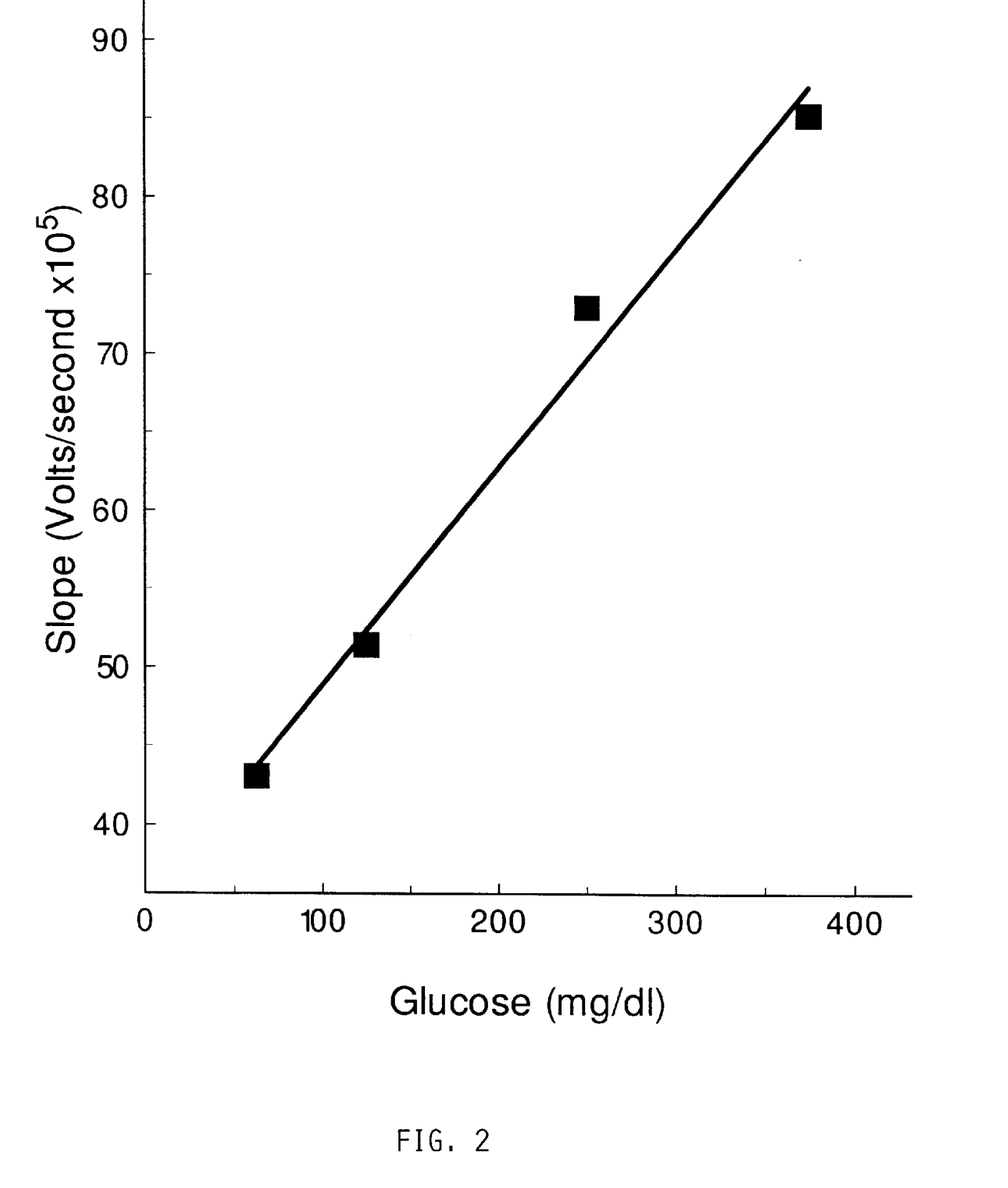
FIG. 2 is a graph illustrating the linearity of fluorescence signal response to various levels of glucose in standard buffer solution for a glucose sensor made as shown in Example 1.

FIG. 2 is a graph illustrating the linearity of fluorescence signal response to various levels of glucose in standard buffer solution for the sensor. The response stabilized after about 20 minutes of testing, and no enzyme loss corresponding to signal loss was observed after about two hours of testing after wet up had occurred.

EXAMPLE 2

Another embodiment of a glucose sensor was made in much the same manner as in Example 1 except that the enzyme layer was prepared by combining 2 g of an aqueous solution of 13% "crosslinker PVOH" (poly(vinyl alcohol), including N-methyl-4(-formalstyryl)pyridinium crosslinking agent) (Polysciences Inc.), 2 mg of glucose oxidase, and 1 g deionized water to form the solution from which the enzyme layer was spin cast onto the oxygen sensing layer-coated substrate as above. The glucose sensors were placed in a UV box for 10 minutes to crosslink the PVOH, removed, and stored under vacuum overnight at room temperature. The sensors were stored in uncovered, Petri dishes in a drawer for three and one half months, whereupon sensor response, wet-up, and stability were tested as above.

Figure 3:
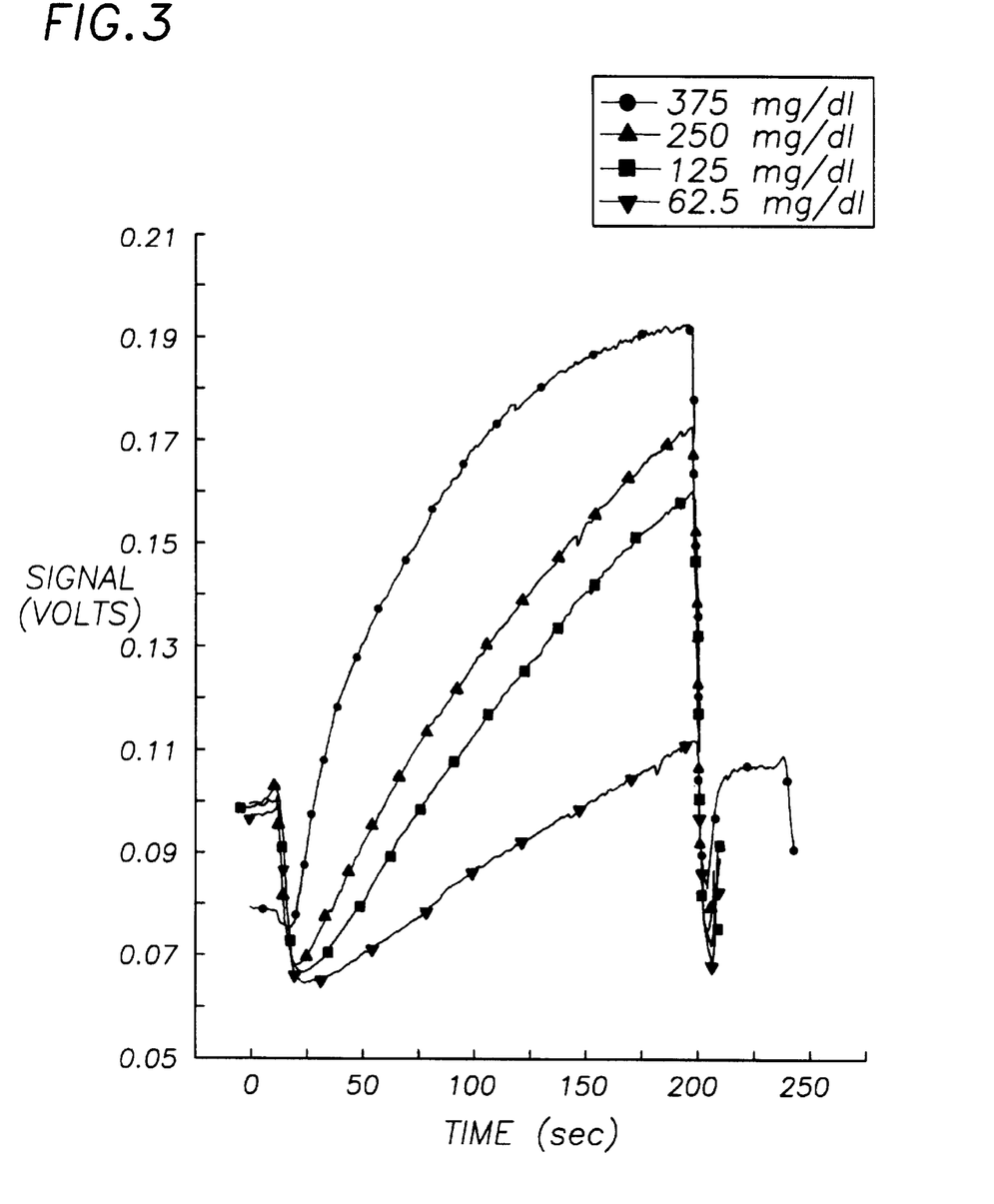
FIG. 3 is a graph illustrating the response of glucose sensors made as shown in Example 2, demonstrating the stability of such sensors after storage.

FIG. 3 illustrates the test results for example 2. Testing was performed with the optical instrument described in FIG. 8. The glucose sensors, despite the storage conditions, showed excellent activity when exposed to varying levels of glucose. The response was found to be comparable to the sensors made in Example 1 and actually a more rapid rate of oxygen uptake per amount of enzyme used was found in comparison to the sensors made with the acrylamide matrix. Also the wet up period was found to be nearly instantaneous as dry sensors gave similarly fast kinetics on the first aqueous sample addition.

EXAMPLE 3

Figure 4:
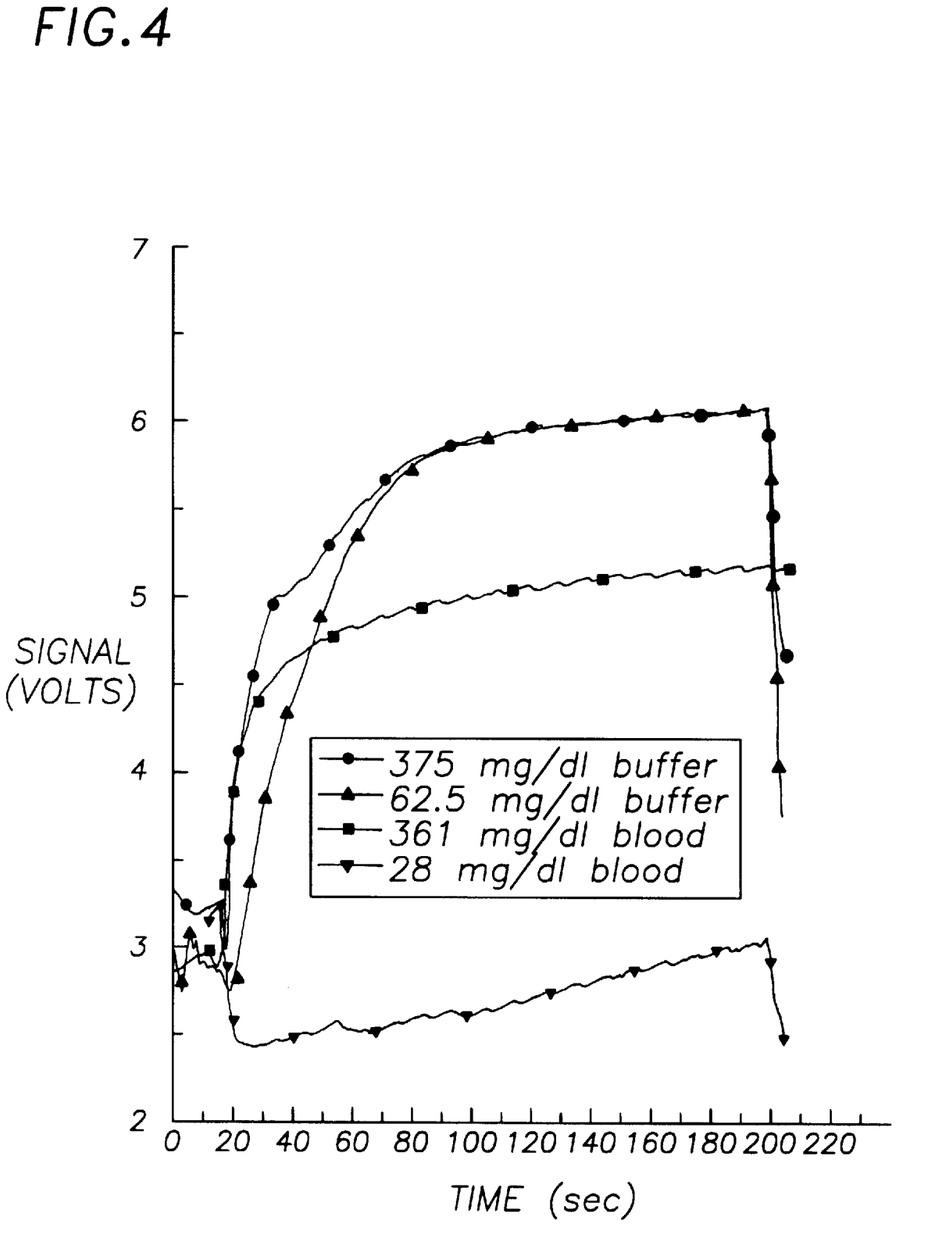
FIG. 4 is a graph comparing the response of glucose sensors, made in accordance with an embodiment of the invention featuring a spacer layer as in Example 3, to blood doped with glucose to give levels near the same concentrations as the standard solutions.

To demonstrate the benefits provided by the spacer layer disclosed herein, the glucose sensors made as in Example 1 were provided with spacer layers as follows. A layer of crosslinked PVOH was laid down in stripes from a solution prepared by mixing 250 mg of the crosslinker PVOH solution with 750 mg of a 5% aqueous solution of PVOH (average molecular weight of the polymer chains 124,000 to 186,000). The stripes were allowed to dry on the benchtop for a few hours before UV curing and vacuum storage. Testing was performed with the optical instrument described in FIG. 8. with a preamplifier 174 sensitivity of 100 pA/V. In this case a single shot protocol was used where a glucose containing blood sample was passed over a hydrated sensor. As illustrated in FIG. 4, blood has very little effect on suppressing the initial response of the glucose sensors when measured within the first half minute. Rather, the increasing glucose level gives rise to an increased rate of oxygen consumption evidenced by the rapidly rising luminescence signal level.

EXAMPLE 4

Figure 5:
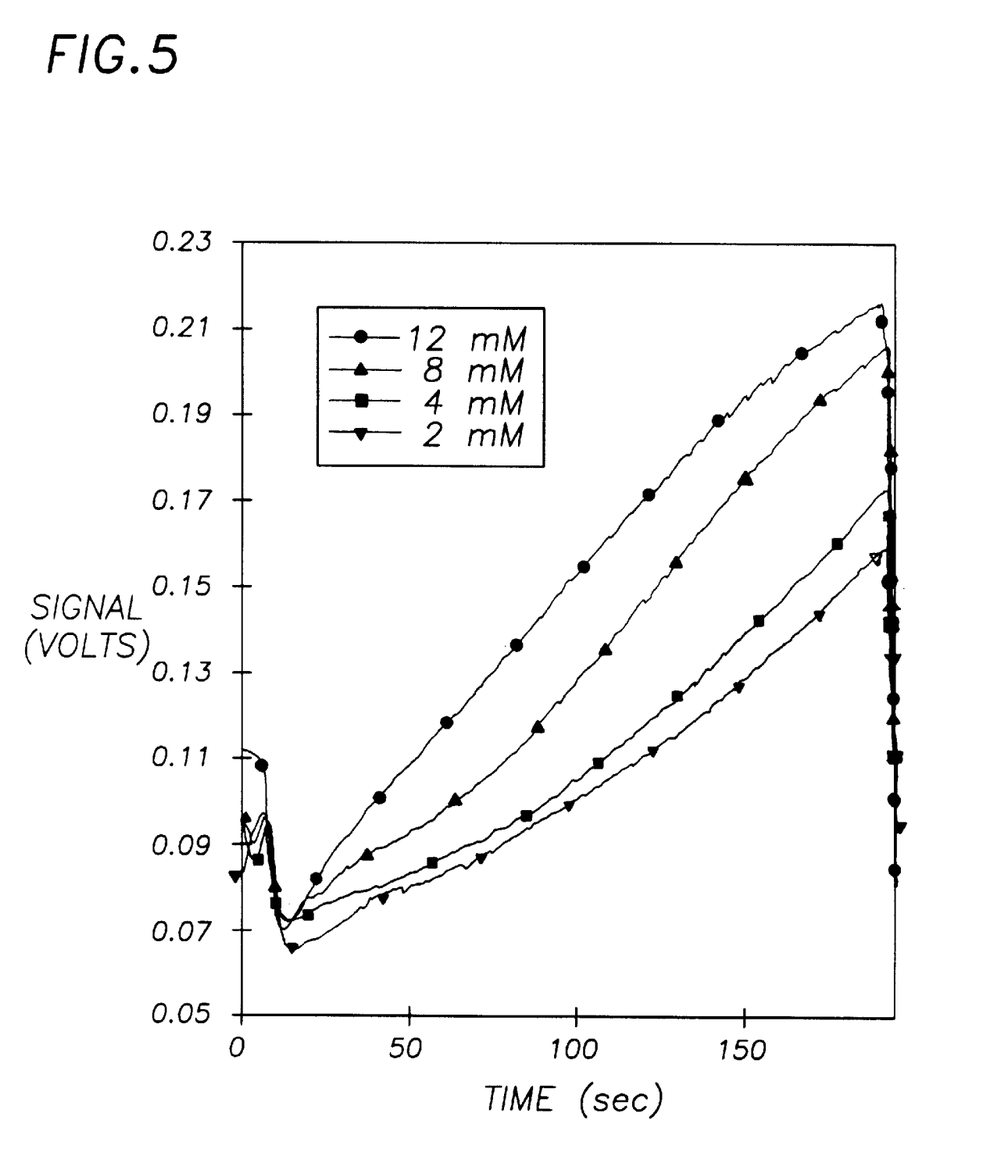
FIG. 5 is a graph illustrating the response of a lactate sensor made as in Example 4.
Figure 6:
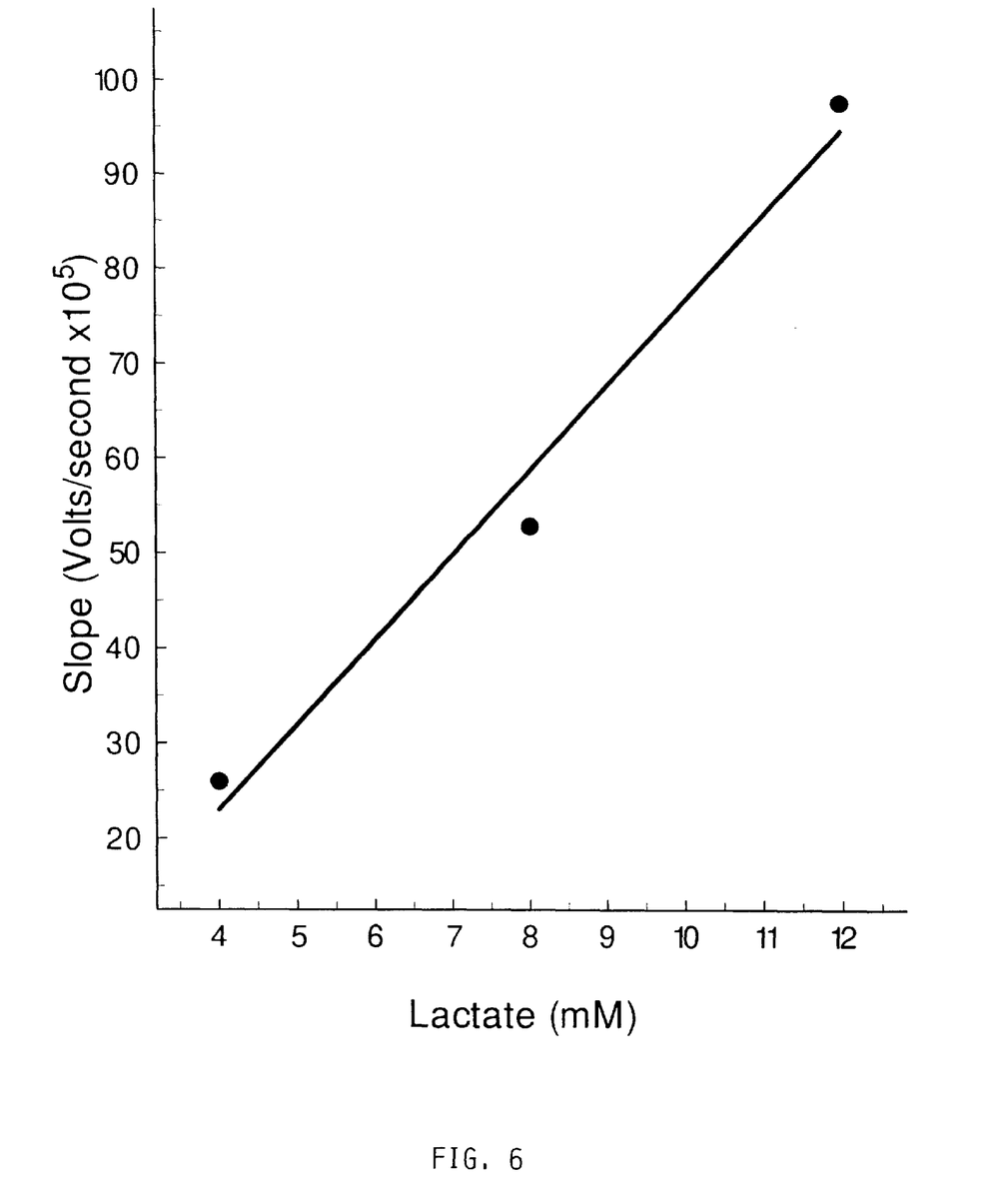
FIG. 6 is a graph illustrating the linearity of fluorescence signal response to various levels of lactate for the lactate sensor of Example 4.

A lactate sensor was made in much the same manner as example 2 above. The enzyme layer solution was prepared by combining 2 g of lactate oxidase, 1 g of crosslinker PVOH solution, 1 g of a 7% aqueous solution of PVOH, and 1 g of deionized water. The sensors were tested as above and the data are presented in FIGS. 5 and 6. FIGS. 5 and 6 demonstrate the good response and linearity of these sensors.

EXAMPLE 5

Figure 7:
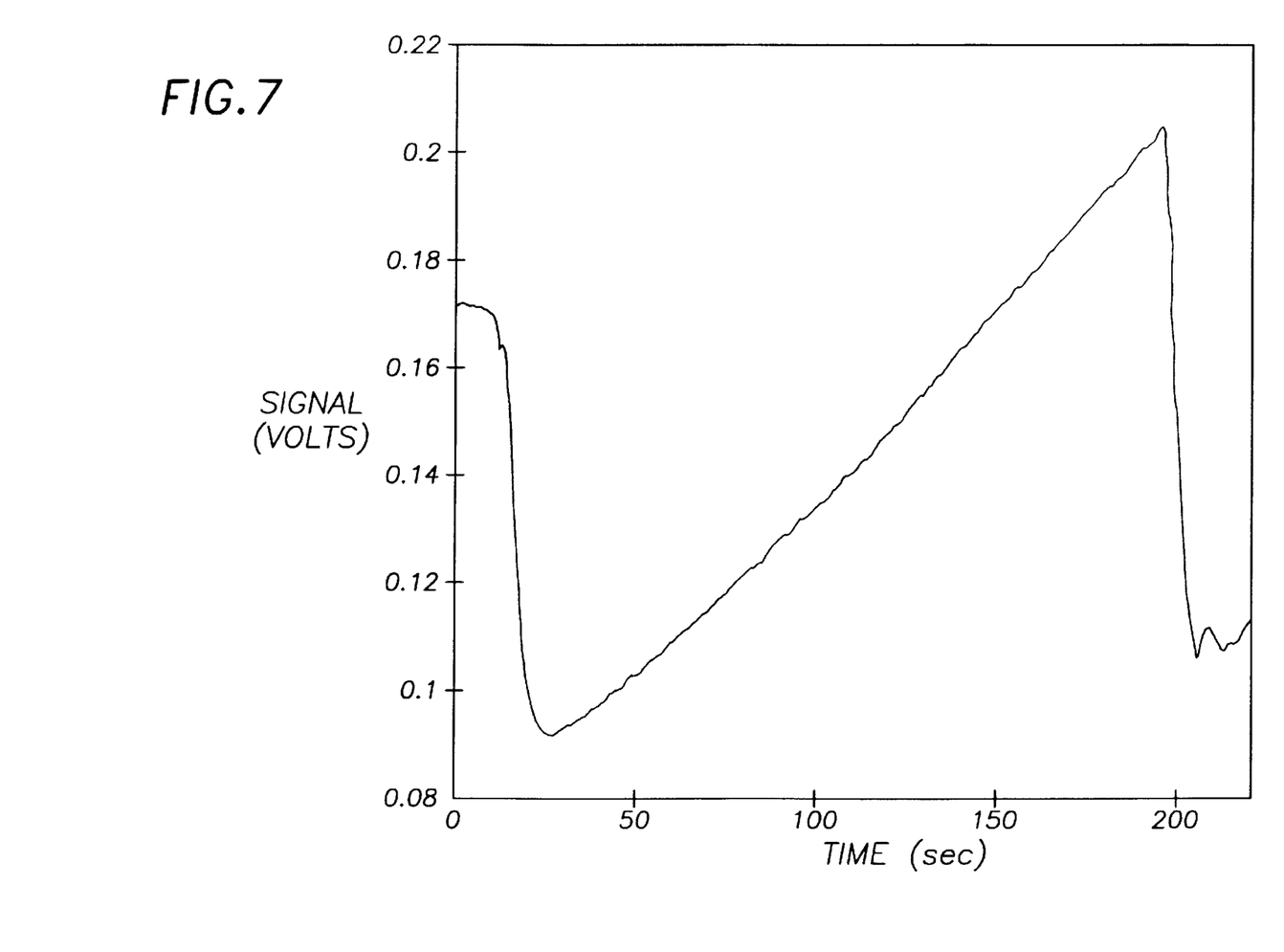
FIG. 7 is a graph illustrating the response of a cholesterol sensor made as shown in Example 5.

Sensors comprising cholesterol oxidase in the enzyme layer were made generally as above to produce a cholesterol sensor. The response curve was measured as above and the data are shown in the graph of FIG. 7.

EXAMPLE 6

Figure 9:
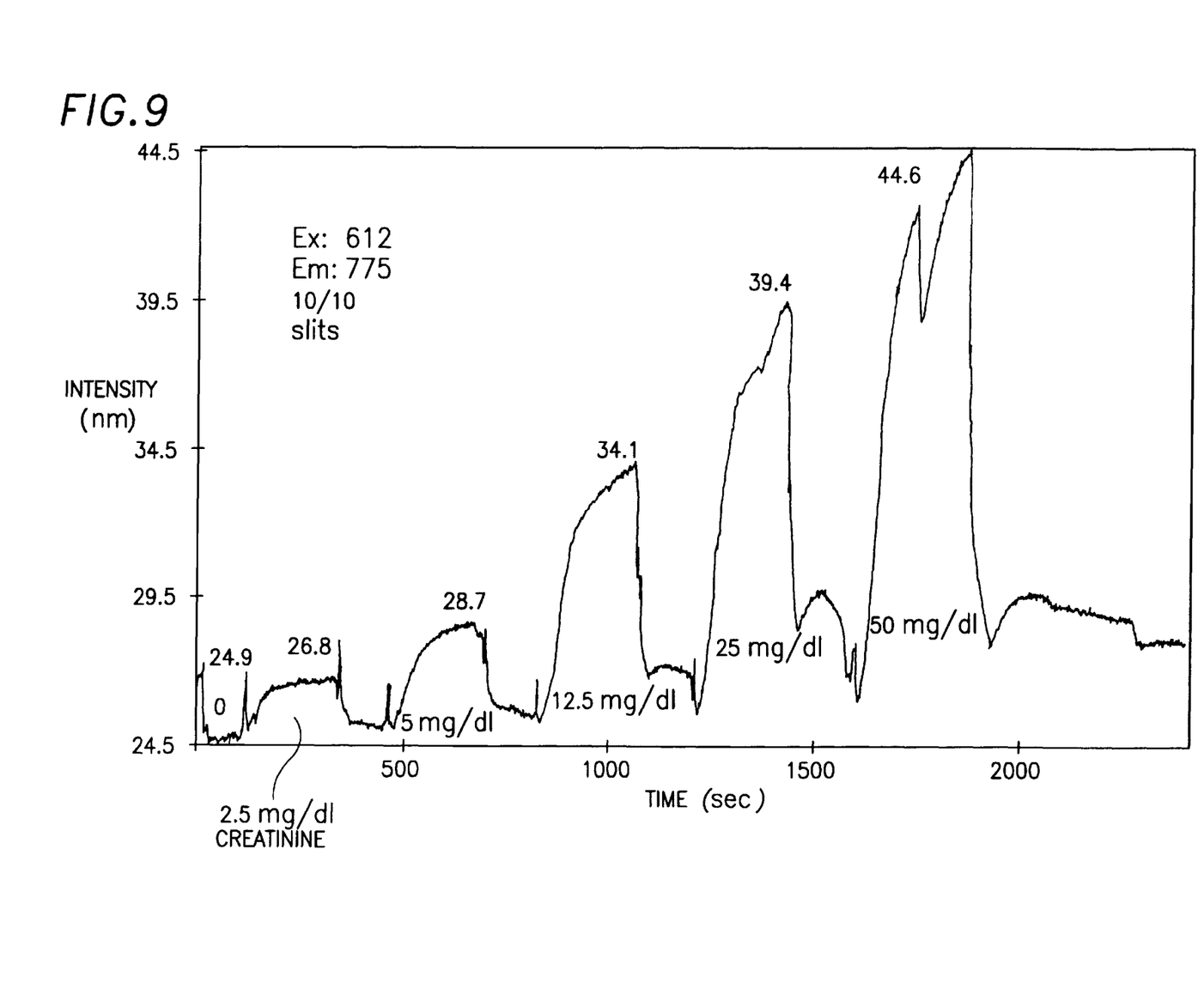
FIG. 9 is a graph illustrating the response of a creatinine sensor made as shown in Example 6.
Figure 10:
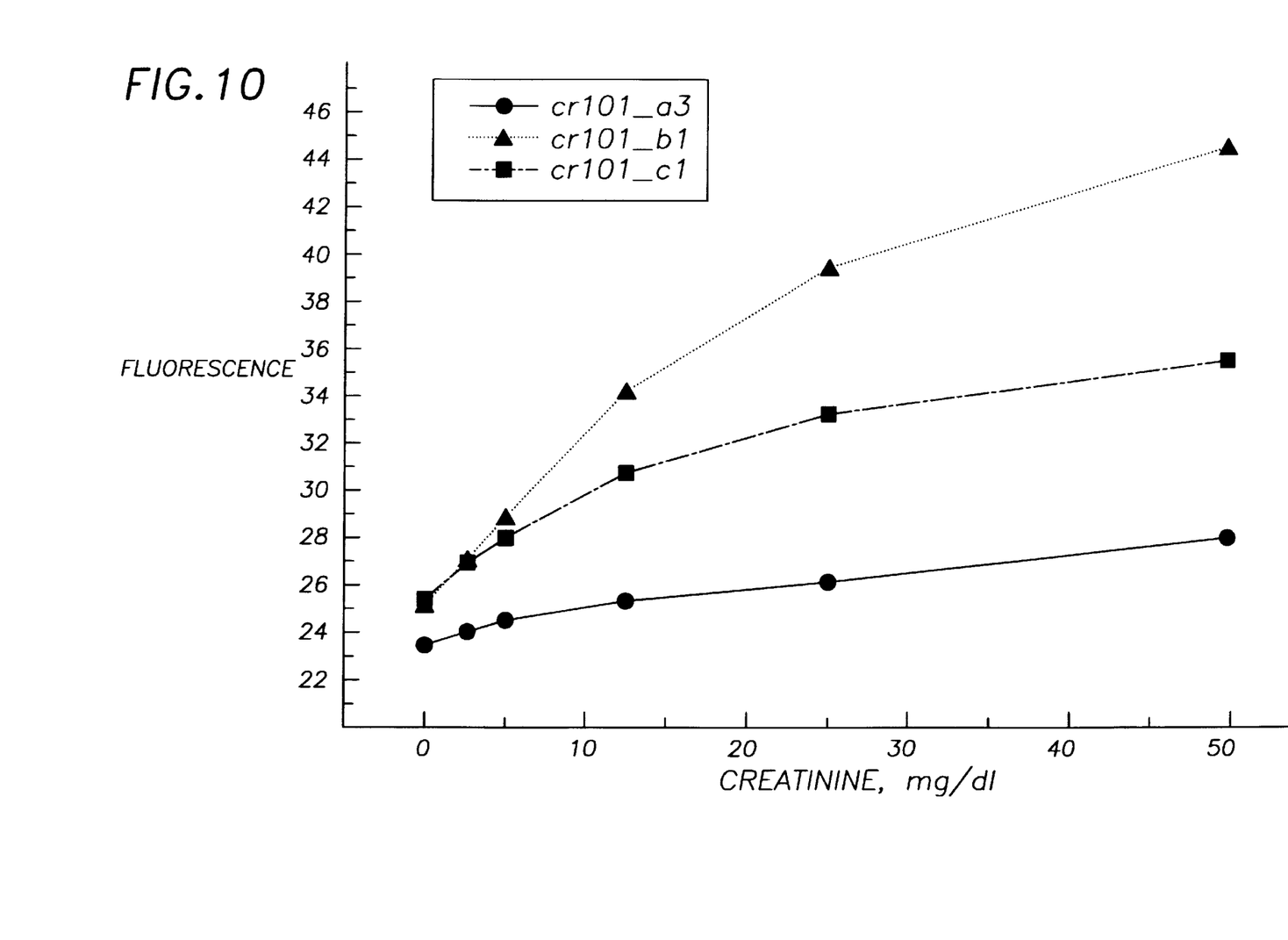
FIG. 10 is a graph illustrating the proportional fluorescence signal response to various levels of creatinine for the creatinine sensors of Example 6.

An optical sensor for measuring creatinine was prepared using the same basic procedures outlined in Examples 1 and 2 for making enzyme sensors except that 2 mg of the dye meso-tetraphenyl-tetrabenzo-Pt-porphyrin (mTPTBP) was substituted in place of octaethyl-Pt-porphyrin (OEP) in making the oxygen sensing layer. A thin oxygen sensing layer was first spin cast as a membrane onto a clear MYLAR® substrate. An enzymatic layer was prepared by adding 13 mg creatinine amidohydrase ("CA"), 20 mg creatine amidinohydrolase ("CI"), and 23 mg sarcosine oxidase ("SO"), to 1 mg of 7% aqueous solution of PVOH. This solution was spin coated onto the oxygen-sensing layer residing on a transparent substrate, and which had been previously prepared. A third spacer or cover layer was spin coated onto the enzymatic layer from a 10% methanol solution of polyhydroxyethylmethacrylate, whereupon the sensor was cured by drying in a fume hood under ambient conditions. The sensors were tested by exposing the sensor to increasing levels of creatinine ranging from 2.5 mg/dl, 5.0 mg/dl, 12.5 mg/dl, 25 mg/dl and finally 50 mg/dl and interspersed with 0.05 M phosphate buffer samples containing no creatinine. The excitation wavelength used for the sensors was 612 nm while the luminous intensity at 775 nm was measured on a model LS50-b Spectrofluorimeter (available from Perkin Elmer, Norwlk Conn.) and equipped with a flow cell to hold the sensors and samples. The actual luminescence response for such a sensor is presented in FIG. 9 and shows that the response is rapid and proportional to increasing levels of creatinine. The plot in FIG. 10 shows the response of several such creatine sensors.

Having thus described certain embodiments of the invention, various alterations, modifications and improvements will readily occur to those skilled in the art. Such alterations, modifications and improvements are intended to be part of this disclosure, and are intended to be within the spirit and scope of the invention. For example, it is contemplated that additional or intervening layers which do not detract from the essential inventive concept are intended to be part of the present invention. Accordingly, the foregoing description is by way of example only and is not intended as limiting. The invention is limited only as defined in the following claims and their equivalents.

What is claimed is:

1. An oxidative enzyme sensor having an optical sensing membrane comprising, in order:
   (a) an enzymatic layer containing an oxidative enzyme in a hydrateable and oxygen permeable matrix;
   (b) an oxygen sensing layer containing luminescent dye in a light-transmissive, oxygen permeable matrix wherein said enzymatic layer is disposed on said oxygen sensing layer, and
   (c) a rapidly hydrating gas-permeable cover layer disposed over the enzymatic layer, wherein the cover layer is effective to delay oxygen released by red blood cells from reaching the oxygen sensing layer for a period of time.

2. The oxidative enzyme sensor of claim 1 further comprising a light-transmissive substrate wherein said oxygen sensing layer is disposed on said light-transmissive substrate.

3. The oxidative enzyme sensor of claim 1 wherein said oxygen sensing layer further comprises a particulate filler material in an effective amount to reduce sample light scattering effects.

4. The oxidative enzyme sensor of claim 2 further comprising a light source and a light detector disposed adjacent said light-transmissive substrate.

5. The oxidative enzyme sensor of claim 1 wherein said enzymatic layer contains an oxidative enzyme specific for substrates selected from the group consisting of glucose, lactate, malate, and cholesterol.

6. The oxidative enzyme sensor of claim 1, wherein said luminescent dye is selected from the group consisting of: ruthenium complexes; porphyrin derivatives; lanthanide complexes; tetrabenzo-Pt-porphyrin; tetraphenyl-Pt-porphyrin; octaethyl-Pt-porphyrin ketone; octaethyl-Pt-porphyrin; octaethyl-Pt-chlorin; tetraphenyl-Pt-chlorin; (4,7-diphenyl-1,1-phenanthroline)$_3$ Ru(II); ligand metal complexes of ruthenium (II), osmium (II), iridium (III), rhodium (III) and chromium (III) ions with 2,2'-bipyridine, 1,10-phenanthroline, 4,7-diphenyl-(1,20-phenanthroline), 4,7-dimethyl-1,10-phenanthroline, 4,7-disulfonated-diphenyl-1,10-phenanthroline, 5-bromo-1,10-phenanthroline, 5-chloro-1,10-phenanthroline, 2-2' bi-2-thiazoline, and 2,2'-bithiazole; meso-tetraphenyl-tetrabenzo-Pt-porphyrin; meso-tetraphenyl-tetrabenzo-Pt-porphyrin (mTPTBP); and tetracyclohexenyl-meso-tetraphenyl-Pt-porphyrin (TCHPP).

7. The oxidative enzyme sensor of claim 3 wherein said particulate filler material is selected from the group consisting of $TiO_2$, zinc oxide, antimony trioxide, barium sulfate, magnesium oxide, and mixtures thereof.

8. The oxidative enzyme sensor of claim 1 wherein said enzymatic layer contains an oxidative enzyme cascade.

9. The oxidative enzyme sensor of claim 8 wherein said oxidative enzyme cascade is specific for creatinine.

10. A method of making an oxidative enzyme sensor having an optical sensing membrane comprising in order:
   (a) preparing an oxygen sensing layer containing a luminescent dye in a light-transmissive, oxygen permeable matrix;
   (b) depositing an enzymatic layer on said oxygen sensing layer, said enzymatic layer containing an oxidative enzyme or oxidative enzyme cascade in an oxygen-permeable matrix; and
   (c) depositing a rapidly hydrating gas-permeable cover layer on the enzymatic layer, wherein the cover layer is effective to delay oxygen released by red blood cells from reaching the oxygen sensing layer for a period of time.

11. The method of claim 10 further comprising the step of disposing said oxygen sensing layer on a light-transmissive substrate.

12. The method of claim 10 wherein said step of preparing further comprises introducing a particulate filler material in an effective amount to reduce sample light scattering effects.

13. The method of claim 10 wherein said step of depositing further comprises depositing said enzymatic layer containing an oxidative enzyme specific for substrates selected from the group consisting of glucose, lactate, and cholesterol.

14. The method of claim 10, wherein said luminescent dye is selected from the group consisting of: ruthenium complexes; porphyrin derivatives; lanthanide complexes; tetrabenzo-Pt-porphyrin; tetraphenyl-Pt-porphyrin; octaethyl-Pt-porphyrin ketone; octaethyl-Pt-porphyrin; octaethyl-Pt-chlorin; tetraphenyl-Pt-chlorin; (4,7-diphenyl-1,1 -phenanthroline)$_3$ Ru(II); ligand metal complexes of ruthenium (II), osmium (II), iridium (III), rhodium (III) and chromium (III) ions with 2,2'-bipyridine, 1,10-phenanthroline, 4,7-diphenyl-(1,20-phenanthroline), 4,7-dimethyl-1,10-phenanthroline, 4,7-disulfonated-diphenyl-1,10-phenanthroline, 5-bromo-1,10-phenanthroline, 5-chloro-1,10-phenanthroline, 2-2' bi-2-thiazoline, and 2,2'-bithiazole; meso-tetraphenyl-tetrabenzo-Pt-porphyrin; meso-tetraphenyl-tetrabenzo-Pt-porphyrin (mTPTBP); and tetracyclohexenyl-meso-tetraphenyl-Pt-porphyrin (TCHPP).

15. The method of claim 12 wherein said step of introducing comprises selecting said particulate filler material from the group consisting of $TiO_2$, zinc oxide, antimony trioxide, barium sulfate, magnesium oxide, and mixtures thereof.

16. The method of claim 10 wherein said step of depositing further comprises depositing said enzymatic layer containing an oxidative enzyme cascade specific for creatinine.

17. The oxidative enzyme sensor of claim 1, wherein the period of time is up to about 30 seconds.

18. The oxidative enzyme sensor of claim 1, wherein the cover layer comprises a crosslinked polymer.

19. The oxidative enzyme sensor of claim 1, wherein the cover layer comprises a polymer is also used to form in part the enzymatic layer.

20. The method of claim 10, wherein the period of time is up to about 30 seconds.

21. The method of claim 10, wherein the cover layer comprises a crosslinked polymer.

22. The method of claim 10, wherein the cover layer comprises a polymer is also used to form in part the enzymatic layer.

* * * * *